United States Patent [19]
Laerum

[11] Patent Number: 5,484,770
[45] Date of Patent: Jan. 16, 1996

[54] PEPTIDE COMPOUNDS WHICH INHIBIT THE PROLIFERATION OF EPIDERMAL OR EPITHELIAL STEM CELLS

[75] Inventor: Ole D. Laerum, Sandviken, Norway

[73] Assignee: Hafslund Nycomed Bioreg AS, Oslo, Norway

[21] Appl. No.: 671,757

[22] PCT Filed: Sep. 13, 1989

[86] PCT No.: PCT/EP89/01071

§ 371 Date: Apr. 8, 1991

§ 102(e) Date: Apr. 8, 1991

[87] PCT Pub. No.: WO90/02753

PCT Pub. Date: Mar. 22, 1990

[30] Foreign Application Priority Data

Sep. 16, 1988 [GB] United Kingdom .................. 8821785

[51] Int. Cl.$^6$ .............................. A61K 38/00; C07K 5/00; C07K 7/00; C07K 17/00
[52] U.S. Cl. .............................. 514/17; 530/329; 530/330; 514/16
[58] Field of Search ........................ 514/16, 17; 530/329, 530/330

[56] References Cited

FOREIGN PATENT DOCUMENTS

| | | |
|---|---|---|
| 0112656 | 7/1984 | European Pat. Off. . |
| 0227410 | 7/1987 | European Pat. Off. . |
| 0267741 | 5/1988 | European Pat. Off. . |
| WO87/00180 | 1/1987 | WIPO . |
| 88/03535 | 5/1988 | WIPO . |

OTHER PUBLICATIONS

Fong et al., *Proc. Natl. Acad. Sci.*, vol. 85, May 1988, pp. 3066–3070.
Laerum et al., *Chemical Abstracts*, vol. 109, Abst No. 36328w 1988.
Kreja et al., *Chem Abstr.*, vol. 105, p. 127, Ab No. 203843m 1986.
Laerum et al., *Chem Abstr.*, vol. 103, Abst No. 194825m 1985.
Foa et al., *Chem Abstr.*, vol. 106, Abst. No. 96321m, 1987.
Bodanszky, *Int. J. Peptide Protein Research*, vol. 25, pp. 449–474, 1985.
Gilman, *Annual Review of Biochemistry*, 56, 610–645, 1987.
Neer, et al., *Nature*, 333, 129–134, 1988.
Snyderman, et al., *Journal of Leukocyte Biology*, 40, 785–800, 1986.
Didsbury, et al., *FEBS Letters*, 219, 259–263, 1987.
Levitsky, *TIBS*, 13, 298–301, 1988.

*Primary Examiner*—Jill Warden
*Assistant Examiner*—A. M. Davenport
*Attorney, Agent, or Firm*—Bacon & Thomas

[57] ABSTRACT

Pentapeptides and derivatives thereof, including derivatives having one or more additional amino acids inserted in the sequence and/or added at the C- and N-termini, have been found to possess good activity in the inhibition of stem cell proliferation.

In addition groups of novel peptides are disclosed, having improved and/or specifically directed inhibitory actions.

12 Claims, No Drawings

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: peptide -continued ( i i i ) HYPOTHETICAL: NO ( i x ) FEATURE:
    ( A ) NAME/KEY: Modified-site
    ( B ) LOCATION: 1
    ( D ) OTHER INFORMATION: /label=pyro
        / note="pyroglutamine"

( x i ) SEQUENCE DESCRIPTION: SEQ ID NO:1:

```
Glu  Glu  Asp  Cys  Lys
1                   5
```

( 2 ) INFORMATION FOR SEQ ID NO:2:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i i i ) HYPOTHETICAL: NO ( i x ) FEATURE:
    ( A ) NAME/KEY: Modified-site
    ( B ) LOCATION: 1
    ( D ) OTHER INFORMATION: /label=Pyro
        / note="Pyroglutamine"

( x i ) SEQUENCE DESCRIPTION: SEQ ID NO:2:

```
Glu  Gln  Asp  Cys  Lys
1                   5
```

( 2 ) INFORMATION FOR SEQ ID NO:3:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i i i ) HYPOTHETICAL: NO ( i x ) FEATURE:
    ( A ) NAME/KEY: Modified-site
    ( B ) LOCATION: 1
    ( D ) OTHER INFORMATION: /label=acyl
        / note="acyl-glutamine"

( x i ) SEQUENCE DESCRIPTION: SEQ ID NO:3:

```
Glu  Glu  Asp  Cys  Lys
1                   5
```

( 2 ) INFORMATION FOR SEQ ID NO:4:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i i i ) HYPOTHETICAL: NO ( i x ) FEATURE:
    ( A ) NAME/KEY: Modified-site
    ( B ) LOCATION: 1
    ( D ) OTHER INFORMATION: /label=pyro
        / note="pyroglutamine"

( x i ) SEQUENCE DESCRIPTION: SEQ ID NO:4:

```
      Glu  Glu  Glu  Cys  Lys
      1                   5
```

( 2 ) INFORMATION FOR SEQ ID NO:5:

( i ) SEQUENCE CHARACTERISTICS:
         ( A ) LENGTH: 5 amino acids
         ( B ) TYPE: amino acid
         ( D ) TOPOLOGY: linear ( i i ) MOLECULE TYPE: peptide ( i i i ) HYPOTHETICAL: NO ( i x ) FEATURE:
         ( A ) NAME/KEY: Modified-site
         ( B ) LOCATION: 1
         ( D ) OTHER INFORMATION: /label=pyro
               / note="pyroglutamine"

( i x ) FEATURE:
         ( A ) NAME/KEY: Modified-site
         ( B ) LOCATION: 5
         ( D ) OTHER INFORMATION: /label=amino
               / note="amidated lysine"

( x i ) SEQUENCE DESCRIPTION: SEQ ID NO:5:

```
      Glu  Glu  Asp  Cys  Lys
      1                   5
```

( 2 ) INFORMATION FOR SEQ ID NO:6:

( i ) SEQUENCE CHARACTERISTICS:
         ( A ) LENGTH: 5 amino acids
         ( B ) TYPE: amino acid
         ( D ) TOPOLOGY: linear ( i i ) MOLECULE TYPE: peptide ( i i i ) HYPOTHETICAL: NO ( i x ) FEATURE:
         ( A ) NAME/KEY: Modified-site
         ( B ) LOCATION: 1
         ( D ) OTHER INFORMATION: /label=pyro
               / note="pyroglutamine"

( x i ) SEQUENCE DESCRIPTION: SEQ ID NO:6:

```
      Glu  Asp  Asn  Cys  Lys
      1                   5
```

( 2 ) INFORMATION FOR SEQ ID NO:7:

( i ) SEQUENCE CHARACTERISTICS:
         ( A ) LENGTH: 6 amino acids
         ( B ) TYPE: amino acid
         ( D ) TOPOLOGY: linear ( i i ) MOLECULE TYPE: peptide ( i i i ) HYPOTHETICAL: NO ( i x ) FEATURE:
         ( A ) NAME/KEY: Modified-site
         ( B ) LOCATION: 1
         ( D ) OTHER INFORMATION: /label=pyro
               / note="pyroglutamine"

( x i ) SEQUENCE DESCRIPTION: SEQ ID NO:7:

```
      Glu  Glu  Asp  Cys  Gly  Lys
      1                   5
```

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 1
        ( D ) OTHER INFORMATION: /label=pyro
            / note="pyroglutamine"

( i x ) FEATURE:
        ( A ) NAME/KEY: Modified-site
        ( B ) LOCATION: 4
        ( D ) OTHER INFORMATION: /label=benzyl
            / note="benzylated cysteine"

( x i ) SEQUENCE DESCRIPTION: SEQ ID NO:8:

Glu    Glu    Asp    Cys    Lys
    1                              5

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 1
        ( D ) OTHER INFORMATION: /label=pyro
            / note="pyroglutamine"

( i x ) FEATURE:
        ( A ) NAME/KEY: Modified-site
        ( B ) LOCATION: 4
        ( D ) OTHER INFORMATION: /label=benzyl
            / note="benzylated cysteine"

( x i ) SEQUENCE DESCRIPTION: SEQ ID NO:9:

Glu    Ala    Asp    Cys    Lys
    1                              5

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 1
        ( D ) OTHER INFORMATION: /label=pyro
            / note="pyroglutamine"

( x i ) SEQUENCE DESCRIPTION: SEQ ID NO:10:

Glu    Ala    Asp    Cys    Lys
    1                              5

(2) INFORMATION FOR SEQ ID NO:11:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:11:

Gln  Glu  Asp  Cys  Lys
    1                           5

(2) INFORMATION FOR SEQ ID NO:12:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (ix) FEATURE:
        (A) NAME/KEY: Modified-site
        (B) LOCATION: 1
        (D) OTHER INFORMATION: /label=pyro
            / note="pyroglutamine"

(xi) SEQUENCE DESCRIPTION: SEQ ID NO:12:

Glu  Glu  Asp  Cys  Gly
    1                           5

(2) INFORMATION FOR SEQ ID NO:13:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (ix) FEATURE:
        (A) NAME/KEY: Modified-site
        (B) LOCATION: 1
        (D) OTHER INFORMATION: /label=pyro
            / note="pyroglutamine"

(ix) FEATURE:
        (A) NAME/KEY: Modified-site
        (B) LOCATION: 4
        (D) OTHER INFORMATION: /label=pyridyl
            / note="2-pyridyl cysteine"

(xi) SEQUENCE DESCRIPTION: SEQ ID NO:13:

Glu  Glu  Asp  Cys  Lys
    1                           5

(2) INFORMATION FOR SEQ ID NO:14:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (ix) FEATURE:
    (A) NAME/KEY: Modified-site
    (B) LOCATION: 1
    (D) OTHER INFORMATION: /label=pyro
        / note="pyroglutamine"

(ix) FEATURE:
    (A) NAME/KEY: Modified-site
    (B) LOCATION: 4
    (D) OTHER INFORMATION: /label=benzyl
        / note="benzylated cysteine"

(xi) SEQUENCE DESCRIPTION: SEQ ID NO:14:

Glu Gly Asp Cys Lys
1                 5

(2) INFORMATION FOR SEQ ID NO:15:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (ix) FEATURE:
    (A) NAME/KEY: Modified-site
    (B) LOCATION: 1
    (D) OTHER INFORMATION: /label=pyro
        / note="pyroglutamine"

(ix) FEATURE:
    (A) NAME/KEY: Modified-site
    (B) LOCATION: 4
    (D) OTHER INFORMATION: /label=benzyl
        / note="benzylated cysteine"

(xi) SEQUENCE DESCRIPTION: SEQ ID NO:15:

Glu Glu Glu Cys Lys
1                 5

(2) INFORMATION FOR SEQ ID NO:16:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (ix) FEATURE:
    (A) NAME/KEY: Modified-site
    (B) LOCATION: 1
    (D) OTHER INFORMATION: /label=pyro
        / note="pyroglutamine"

(xi) SEQUENCE DESCRIPTION: SEQ ID NO:16:

Glu Gly Asp Phe Lys
1                 5

(2) INFORMATION FOR SEQ ID NO:17:

(i) SEQUENCE CHARACTERISTICS:
        (A) LENGTH: 5 amino acids
        (B) TYPE: amino acid
        (D) TOPOLOGY: linear ( i i ) MOLECULE TYPE: peptide ( i i i ) HYPOTHETICAL: NO ( i x ) FEATURE:
    ( A ) NAME/KEY: Modified-site
    ( B ) LOCATION: 1
    ( D ) OTHER INFORMATION: /label=pyro
        / note="pyroglutamine"

( x i ) SEQUENCE DESCRIPTION: SEQ ID NO:17:

Glu Gly Asn Cys Lys
1                      5

( 2 ) INFORMATION FOR SEQ ID NO:18:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 1
        ( D ) OTHER INFORMATION: /label=pyro
            / note="pyroglutamine"

( x i ) SEQUENCE DESCRIPTION: SEQ ID NO:18:

Glu Gln Asn Cys Lys
1                      5

( 2 ) INFORMATION FOR SEQ ID NO:19:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 1
        ( D ) OTHER INFORMATION: /label=pyro
            / note="pyroglutamine"

( x i ) SEQUENCE DESCRIPTION: SEQ ID NO:19:

Glu Glu Asp Ser Lys
1                      5

( 2 ) INFORMATION FOR SEQ ID NO:20:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 1
        ( D ) OTHER INFORMATION: /label=pyro
            / note="pyroglutamine"

( x i ) SEQUENCE DESCRIPTION: SEQ ID NO:20:

Glu Gly Asp Cys Lys
1               5

( 2 ) INFORMATION FOR SEQ ID NO:21:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( i i i ) HYPOTHETICAL: NO ( i x ) FEATURE:
( A ) NAME/KEY: Modified-site
( B ) LOCATION: 1
( D ) OTHER INFORMATION: /label=pyro
/ note="pyroglutamine"

( x i ) SEQUENCE DESCRIPTION: SEQ ID NO:21:

Glu Asp Asp Cys Lys
1               5

( 2 ) INFORMATION FOR SEQ ID NO:22:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( i i i ) HYPOTHETICAL: NO ( i x ) FEATURE:
( A ) NAME/KEY: Modified-site
( B ) LOCATION: 1
( D ) OTHER INFORMATION: /label=pyro
/ note="pyroglutamine"

( x i ) SEQUENCE DESCRIPTION: SEQ ID NO:22:

Glu Asp Asp Cys Lys
1               5

( 2 ) INFORMATION FOR SEQ ID NO:23:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( i i i ) HYPOTHETICAL: NO ( x i ) SEQUENCE DESCRIPTION: SEQ ID NO:23:

Glu Glu Asp Cys Lys
1               5

( 2 ) INFORMATION FOR SEQ ID NO:24:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide (i i i) HYPOTHETICAL: NO (x i) SEQUENCE DESCRIPTION: SEQ ID NO:24:

Pro Glu Asp Cys Lys
1               5

(2) INFORMATION FOR SEQ ID NO:25:

(i) SEQUENCE CHARACTERISTICS:
      (A) LENGTH: 5 amino acids
      (B) TYPE: amino acid
      (D) TOPOLOGY: linear (i i) MOLECULE TYPE: peptide (i i i) HYPOTHETICAL: NO (i x) FEATURE:
      (A) NAME/KEY: Modified-site
      (B) LOCATION: 1
      (D) OTHER INFORMATION: /label=pyro
         / note="pyroglutamine"

(x i) SEQUENCE DESCRIPTION: SEQ ID NO:25:

Glu Glu Glu Cys Arg
1               5

(2) INFORMATION FOR SEQ ID NO:26:

(i) SEQUENCE CHARACTERISTICS:
      (A) LENGTH: 6 amino acids
      (B) TYPE: amino acid
      (D) TOPOLOGY: linear (i i) MOLECULE TYPE: peptide (i i i) HYPOTHETICAL: NO (x i) SEQUENCE DESCRIPTION: SEQ ID NO:26:

Ser Glu Glu Glu Cys Arg
1               5

(2) INFORMATION FOR SEQ ID NO:27:

(i) SEQUENCE CHARACTERISTICS:
      (A) LENGTH: 6 amino acids
      (B) TYPE: amino acid
      (D) TOPOLOGY: linear (i i) MOLECULE TYPE: peptide (i i i) HYPOTHETICAL: NO (x i) SEQUENCE DESCRIPTION: SEQ ID NO:27:

Ser Gln Glu Glu Cys Arg
1               5

(2) INFORMATION FOR SEQ ID NO:28:

(i) SEQUENCE CHARACTERISTICS:
      (A) LENGTH: 5 amino acids
      (B) TYPE: amino acid
      (D) TOPOLOGY: linear (i i) MOLECULE TYPE: peptide (i x) FEATURE:
      (A) NAME/KEY: Modified-site
      (B) LOCATION: 1
      (D) OTHER INFORMATION: /label=pyro
         / note="pyroglutamine"

( x i ) SEQUENCE DESCRIPTION: SEQ ID NO:28:

Glu Glu Asp Cys Lys
1               5

( 2 ) INFORMATION FOR SEQ ID NO:29:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=pyro
            / note="pyroglutamine"

( x i ) SEQUENCE DESCRIPTION: SEQ ID NO:29:

Glu Glu Asp Cys Ala Lys
1               5

( 2 ) INFORMATION FOR SEQ ID NO:30:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:30:

Lys Ile Ile His Glu Asp Gly Tyr Ser
1               5

( 2 ) INFORMATION FOR SEQ ID NO:31:

( i ) SEQUENCE CHARACTERISTICS:
    ( A ) LENGTH: 17 amino acids
    ( B ) TYPE: amino acid
    ( D ) TOPOLOGY: linear ( i i ) MOLECULE TYPE: peptide ( i x ) FEATURE:
    ( A ) NAME/KEY: Region
    ( B ) LOCATION: 10..15
    ( D ) OTHER INFORMATION: /label=peptide
            / note="Denotes the peptide Ra-Rb-Rc-Rd-Re-Rf as
            defined in Formula I"

( x i ) SEQUENCE DESCRIPTION: SEQ ID NO:31:

Lys Ile Ile His Glu Asp Gly Tyr Ser Xaa Xaa Xaa Xaa Xaa
1               5                   10

Xaa Gln Tyr
15

( 2 ) INFORMATION FOR SEQ ID NO:32:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site (B) LOCATION: 1
(D) OTHER INFORMATION: /label=pyro
/ note="pyroglutamine"

(xi) SEQUENCE DESCRIPTION: SEQ ID NO:32:

Glu Glu Asp Phe Lys
1               5

(2) INFORMATION FOR SEQ ID NO:33:

(i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=pyro
/ note="pyroglutamine"

(xi) SEQUENCE DESCRIPTION: SEQ ID NO:33:

Glu Gly Asp Cys Lys
1               5

(2) INFORMATION FOR SEQ ID NO:34:

(i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=pyro
/ note="pyroglutamine"

(xi) SEQUENCE DESCRIPTION: SEQ ID NO:34:

Glu Asp Glu Ser Lys
1               5

(2) INFORMATION FOR SEQ ID NO:35:

(i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=pyro
/ note="pyroglutamine"

(xi) SEQUENCE DESCRIPTION: SEQ ID NO:35:

Glu Glu Glu Ser Lys
1               5

PEPTIDE COMPOUNDS WHICH INHIBIT THE PROLIFERATION OF EPIDERMAL OR EPITHELIAL STEM CELLS

The present invention relates to the use of peptides having an inhibitory effect on cell proliferation, and to novel peptides having specific and/or general inhibitory effects.

The mammalian body contains cells having enormously diverse structures and functions, and the mechanisms of differentiation and development have been the focus of much study. It is known that for systems of cells having a continuous turnover the mechanism commonly involves a reservoir of pluripotent stem cells which divide and constantly supply new cells to the system. While initially homogeneous the stem cells supplied from the "reservoir" soon become committed to one or other morphology and subsequently develop into the required functional cells.

Examples of such stem cell systems are the haemopoietic system in bone marrow and the epithelial and epidermal systems.

It has previously been reported that peptides corresponding to a narrow general formula can inhibit haemopoiesis (see EP-A-0112656), while a group of dimeric peptides corresponding to a slightly broader general formula and linked by a disulphide bridge could stimulate haemopoiesis (see WO88/03535). It was stated in both cases, however, that no effects were observed on systems other than haemopoiesis.

We have now surprisingly found that a class of peptides, including certain of the peptides disclosed in EP-A-0112656, have a more general ability to inhibit cell proliferation, and that minor modifications to the amino-acid sequence and/or blocking of critical side-chain residues can direct the action of the peptides to specific systems of interest.

Our findings have been based on the observation that certain of the pentapeptide sequences disclosed in our above patent applications occurred in certain so-called G-proteins, namely $G_{\alpha i}$ proteins. The G proteins are found on the interior side of cell membranes and provide an essential link between transmembrane receptors and effectors located near the G proteins inside the cell. They are involved in many cell functions, according to the effectors with which they are linked. They consist of 3 linked sub-units $\alpha$, $\beta$ and $\gamma$, the $\alpha$ sub-unit being involved in activating the adjacent effector. The G proteins were initially characterised by their function and the sub-class of $G_i$ proteins are those originally found to inhibit adenylate cyclase. This finding led to the consideration of the role of the peptides in inhibition of proliferation of the epithelial and epidermal systems and cell systems generally.

Thus according to the invention we provide the use of compounds of formula (I)

$$R^a\text{---}R^b\text{---}R^c\text{---}R^d\text{---}(R^e)_n\text{---}R^f \quad (I)$$

wherein $R^a$ represents

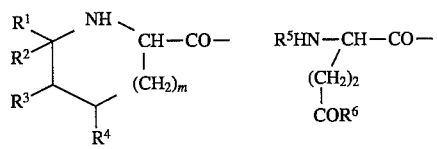

$R^b$ represents

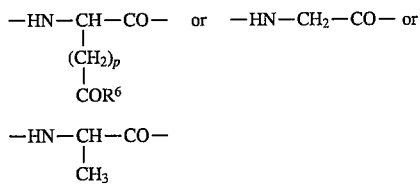

$R^c$ represents

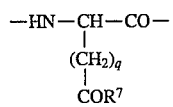

$R^d$ represents

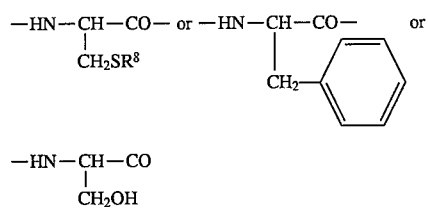

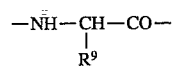

$R^e$ represents

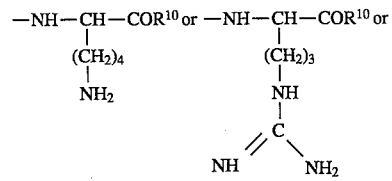

and $R^f$ represents

—NH—CH$_2$—COR$^{10}$ (wherein n and m independently represent 0 or 1;

p and q independently represent 1 or 2;

$R^1$ and $R^2$ are both hydrogen atoms or together represent an oxo group;

$R^3$ and $R^4$ are both hydrogen atoms or together represent a carbon—carbon bond;

$R^5$ is hydrogen or an acyl group;

$R^6$ and $R^7$ independently represent a hydroxy group or an amino group, $R^8$ represents hydrogen; a $C_{2-6}$ alkyl group; a $C_{7-20}$ aralkyl group, which may carry one or more hydroxy, amino or methoxy substituents; or a metabolically labile S-protecting group;

$R^9$ represents hydrogen or a methyl group;

$R^{10}$ represents a hydroxy or amino group, the residue of the amino acid glutamine or a peptide having an N-terminal glutamine unit;

and apart from alanine, which may be in the D or L form, and glycine, all the said amino acid residues are in the L-form)

in the preparation of a medicament for the inhibition of non-haemopoietic cell proliferation.

Where an N-terminal protecting group $R^5$ is present this may, as indicated above, be an acyl group having 1–20 carbon atoms, e.g. a lower alkanoyl group having 1–5 carbon atoms such as the acetyl group, or an aroyl or aralkanoyl group having 7 to 20 carbon atoms such as the benzoyl or phenylacetyl group.

$R^5$ may also be an acyl group derived from an amino acid or a peptide chain. In particular, $R^5$ may be an acyl group derived from serine or any of the peptides derived from the following amino acid sequence by removal of successive N-terminal amino acids: Lys-Ile-Ile-His-Glu-Asp-Gly-Tyr-Ser.

As explained in detail hereinafter, peptides having the above sequence or part thereof have a high level of homology with $G_{i\alpha}$ proteins which are known to control a number of cell functions including inhibition of growth. The terminal amino group of the overall peptide of formula (I) is preferably protected, e.g. by acylation with an alkanoyl, aralkanoyl or aroyl group.

Where $R^8$ is a $C_{2-6}$ alkyl group this may, for example, be an ethyl, butyl or hexyl group. When $R^8$ is an aralkyl group, this may conveniently be an arylmethyl group such as benzyl, diphenylmethyl or triphenylmethyl. Where $R^8$ is a metabolically labile group this may, for example, be an arylthio group having 5 to 10 carbon atoms, e.g. the pyridyl thio group, or an acyl group as defined above.

The compounds of the invention are preferably pentapeptides, that is n is preferably 0.

The cyclic groups in the $R^a$ residue are preferably five-membered, that is m is preferably 0.

The abiliity of the pentapeptides of the invention to inhibit proliferation of a wide range of cells in addition to or even excluding the haemopoietic system is of value in medicine either where excessive cell proliferation requires treatment, as in psoriasis, or where cancer therapy would be likely to damage a particular cell population. Many cell types are particularly susceptible to the cytotoxic drugs or radiations used in anti-cancer therapy and one known technique is to use a drug to inhibit proliferation of cells such as those of the haemopoietic system during the anti-cancer therapy, followed by resumption of normal proliferation when the effect of the inhibitory drug has disappeared. The peptides of the present invention appear to have appropriately short biological half-lives for such therapy. Similarly, proliferation of selected populations of cells susceptible to cancer therapy may be inhibited together with the cancer cells themselves and the anti-cancer therapy is initiated only when the cancer cells have reached a susceptible phase of proliferation while the normal cells are in a less susceptible phase.

One type of cell proliferation occurs when cells such as bone marrow cells, phagocytes or granulocytes are stimulated by CSF drugs during therapy. Inhibition of cell growth can restore such cells to normal growth rates.

In many autoimmune diseases, the subject produces leucocytes active against their own tissues. By inhibiting leucocyte function, at least for a time, such autoimmune reactions may be correspondingly reduced.

By becoming involved in the $G_{\alpha i}$ protein transcellular signalling mechanism, other functions controlled by $G_{\alpha i}$ proteins may be modfied by the active peptides, for example calcium metabolism cell mobility and cytoplasmic cellular processes mediated by the $G_{\alpha i}$ protein.

Thus the invention also provides novel polypeptides containing full or partial sequences substantially homologous with the $G_{\alpha i}$ proteins discussed above, namely —Lys-Ile-Ile-His-Glu-Asp-Gly-Tyr-Ser-$R^{a'}$-$R^b$-$R^c$-$R^dR^e$-$R^f$-Gln-Tyr— or parts thereof or slight variations thereof such as those described in Ann. Rev. Biochem. 56 pp. 624–625 (1987) and Proc. Natl. Acad. Sci. USA 85 PP. 3066–3070 (1988). Such sequences preferably contain at least one Tyr residue to aid labelling of the polypeptides. As indicated below, the N-terminal $NH_2$ is preferably protected e.g. by N-acylation as discussed above. Where the N-terminal amino acid residue would be Glu in such a homologous sequence, this may also advantageously be replaced by p-Glu.

Such polypeptides will be referred to as compounds of formula (Ia) and can be represented as compounds of formula (I) as defined above wherein $R^5$ is an acyl group derived from the residue of the amino acid serine or a peptide chain having a C-terminal serine unit and/or $R^{10}$ is the residue of the amino acid glutamine or a peptide having an N-terminal glutamine unit. They preferably contain a total of up to 12 amino acid residues, more preferably 10 or fewer.

In general it is preferred that the N-terminal $NH_2$ of any added peptide sequence should be protected, e.g. by acylation. This assists in avoiding enzymatic degradation of the peptide. Most of the $R^a$ residues permitted for formula (I) are not suitable for amino acid addition without deprotection or similar conversion to residues having a free $NH_2$ group. Thus, where $R^5$ is an acyl group other than an acyl group derived from an amino acid or peptide, deacylation will be required. Similarly, where $R^1$ and $R^2$ together form an oxo group, as in p-Glu units, conversion to a corresponding open chain residue such as Glu or Gln is required.

The invention thus utilises the effects of the peptides on cytoplasmic cellular processes mediated by the $G_{\alpha i}$- protein.

Only the compounds described in our earlier European Patent Specification No. 112656 have been described previously as having any use in medicine. All the other compounds of formula I as defined above are either novel or have only been described as intermediates. According to a further feature of the invention, therefore, we provide compounds of formula (I) as defined above, other than

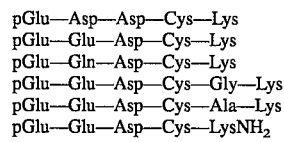

for use as agents for controlling cell proliferation.

Certain selected peptides from within the above formula (I) are novel and have been found to possess particularly desirable combinations of properties. Thus according to one aspect of the invention we provide compounds of formula

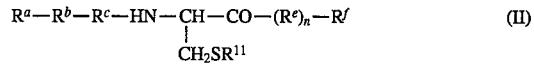

wherein $R^a$, $R^b$, $R^c$, $R^e$, $R^f$ and n are as defined for formula I, $R^{11}$ is a $C_{2-6}$ alkyl or a $C_{7-20}$ aralkyl group which may carry one or more hydroxy, amino or methyl substituents, and all amino acids are in the chiral form stated for formula (I). Particularly preferred compounds according to this formula are

and

Compounds having a blocked cystein residue of this type have been found to have improved stability in vivo and sustained activity in cell proliferation inhibition.

Analogues of the above-mentioned benzyl-cystein compounds can be made wherein the phenyl-substitution is less labile, such compounds possessing a phenylalanine residue instead of the cystein residue at the 4-position. Thus according to a further aspect of the invention we provide compounds of formula

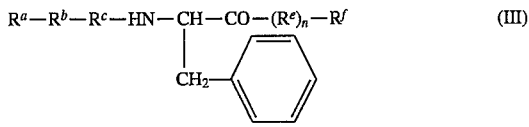

wherein $R^a$, $R^b$, $R^c$, $R^e$, $R^f$, and n are as defined for formula I and all amino acids are in the chiral form stated for formula (I) Such compounds also have sustained in vivo activity, and particularly preferred examples are pGlu-Glu-Asp-Phe-Lys and pGlu-Gly-Asp-Phe-Lys.

By contrast it is also possible to prepare peptides having a metabolically labile blocking group so that slow release of the unblocked peptide can be achieved in vivo. Thus according to a further aspect of the invention we provide compounds of formula

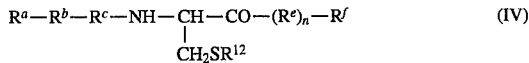

wherein $R^a$, $R^b$, $R^c$, $R^e$, $R^f$ and n are as defined for formula I, $R^{12}$ is a metabolically labile group, for example a 2-pyridylthio group, and all amino acids have the chiral form stated for formula (I). A preferred compound is pGlu-Glu-Asp-(2-Pyridyldithiocys)-Lys which has been found to have a delayed inhibitory effect on haemopoiesis, occurring after 3 days in vivo compared to 1 day for the unblocked analogue.

Inhibition of leucocyte function (including the immune system) in addition to haemopoiesis can be achieved by slight modifications of the amino acid sequence, specifically by replacement of $Glu^2$ by $Gly^2$. Thus according to a further feature of the invention we provide compounds of formula

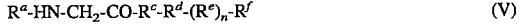

wherein $R^a$, $R^c$, $R^d$, $R^e$, $R^f$ and n are as defined for formula (I) and all the amino acid residues have the chiral form stated for formula (I). Preferred compounds of this formula are pGlu-Gly-Asp-Phe-Lys and pGlu-Gly-Asp-Cys-Lys, the latter of which has been found to inhibit migration of granulocytes and macrophages in vivo (by formation of a skin window in guinea pigs and local BCG stimulation) and uptake of *staphylococcus aureus* by granulocytes in vitro (as measured by flow cytometry), in addition to its haemopoietic inhibitory effects.

A group of peptides wherein the haemopoietic inhibitory effects are completely, absent, and are replaced by inhibition of epidermal and epithelial cell proliferation, can be made by replacement of the cystein residue at position 4 by a serine residue. Such compounds according to the invention have the formula

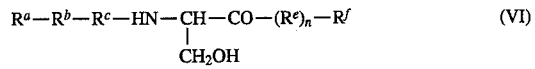

wherein $R^a$, $R^b$, $R^c$, $R^e$, $R^f$ and n are as defined for formula I and all amino acids have the chiral forms stated for formula (I); preferred compounds are pGlu-Glu-Asp-Ser-Lys pGlu-Asp-Glu-Ser-Lys and pGlu-Glu-Glu-Ser-Lys.

These compounds are of great utility in the inhibition of non-haemopoietic cell proliferation during selected cytostatic treatment of malignant haemopoietic cells, and also in the suppression of malignant epidermal and epithelial cells which occur for instance in advanced cases of squamous carcinomas and psoriasis.

Finally it is possible to use the peptides according to the invention to "target" other molecules by coupling of the molecule to the peptide chain. Accordingly we provide (a) compounds for use in therapy, diagnosis or assay comprising a radioisotope or radiolabelled ligand covalently linked directly or indirectly to a peptide according to the invention;

(b) compounds for use in therapy comprising a cytotoxic ligand covalently linked to a peptide according to the invention; and (c) compounds for use in diagnosis or assay comprising a fluorochromic ligand covalently linked to a peptide according to the invention.

In general, in order to exert a protective effect against cytotoxic drugs, the peptides of the invention may be administered to human patients by injection in the dose range 1–10 ng, for example 4–5 ng, per 70 kg body weight per day. If administered by infusion or similar techniques, the dose may be in the range 30–300 ng per 70 kg body weight, for example about 100 ng, over six days. In principle it is desirable to produce a concentration of the peptide of about $10^{-11}$M to $10^{-7}$M in the extracellular fluid of the patient.

In general, combined therapy with cytotoxic drugs such as cytosine arabinoside requires careful timing to ensure that the myelopoietic system is protected while the cytotoxic drug is still present.

According to a still further feature of the present invention there are provided pharmaceutical compositions comprising as active ingredient at least one compound of formula (Ia), (II), (III), (IV), (V) or (VI) as hereinbefore defined or a physiologically compatible salt thereof, in association with a pharmaceutical carrier or excipient. The compositions according to the invention may be presented, for example, in a form suitable for oral, nasal, parenteral or rectal administration.

As used herein, the term "pharmaceutical" includes veterinary applications of the invention.

The compounds according to the invention may be presented in the conventional pharmacological forms of administration, such as tablets, coated tablets, nasal sprays, solutions, emulsions, powders, capsules or sustained release forms. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Injection solutions may, for example, be produced in the conventional manner, such as by the addition of preservation agents, such as p-hydroxybenzoates, or stabilizers, such as EDTA. The solutions are then filled into injection vials or ampoules. Delayed release injection may be provided by so-called minipumps.

Nasal sprays may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the compounds of this invention preferably contain 1–10 mg, for example 4–5 mg of the peptide.

The peptides of the invention may be synthesised in any convenient way. In general, the reactive side chain groups present (amino, thiol and/or carboxyl) will be protected during the coupling reactions of the overall synthesis but it is possible to leave some side chain groups unprotected (hydroxy groups, imidazole groups, primary amide groups, amide groups in cyclic amino acids like pyroGlu) during the entire synthetic procedure.

The final step will thus be the deprotection of a fully protected or a partly protected derivative of a peptide of the general formula I and such processes form a further aspect of the invention.

In building up the peptide chains, one can in principle start either at the C-terminal or the N-terminal although only the C-terminal starting procedure is in common use.

Thus, one can start at the C-terminal by reaction of a suitably protected derivative of, for example lysine with a suitable protected derivative of cysteine. The lysine derivative will have a free α-amino group while the other reactant will have either a free or activated carboxyl group and a protected amino group. After coupling, the intermediate may be purified for example by chromatography, and then selectively N-deprotected to permit addition of a further N-protected and free or activated amino acid residue. This procedure is continued until the required amino acid sequence is completed.

Carboxylic acid activating substituents which may, for example, be employed include symmetrical or mixed anhydrides, or activated esters such as for example p-nitrophenyl ester, 2,4,5,-trichlorophenylester, N-hydroxybenzotriazole ester (OBt), N-hydroxysuccinimidylester (OSu) or pentafluorophenylester (OPFP).

The coupling of free amino and carboxyl groups may, for example, be effected using dicyclohexylcarbodiimide (DCC). Another coupling agent which may, for example, be employed is N-ethoxycarbonyl-2-ethoxy- 1,2-dihydroquinoline (EEDQ).

In general it is convenient to effect the coupling reactions at low temperatures, for example, −20° C. up to ambient temperature, conveniently in a suitable solvent system, for example, tetrahydrofuran, dioxan, dimethylformamide, methylene chloride or a mixture of these solvents.

It may be more convenient to carry out the synthesis on a solid phase resin support. Chloromethylated polystyrene (cross-linked with 1% divinyl benzene) is one useful type of support; in this case the synthesis will start the C-terminal, for example by coupling N-protected lysine to the support.

A number of suitable solid phase techniques are described by Eric Atherton, Christopher J. Logan, and Robert C. Sheppard, J. Chem. Soc. Perkin I, 538–46 (1981); James P. Tam, Foe S. Tjoeng, and R. B, Merrifield J. Am. Chem. Soc. 102, 6117–27 (1980); James P. Tam, Richard D. Dimarchi and R. B. Merrifield Int. J. Peptide Protein Res 16 412–25 (1980); Manfred Mutter and Dieter Bellof, Helvetica Chimica Acta 67 2009–16 (1984)

A wide choice of protecting groups for amino acids are known and are exemplified in Schröder, E., and Lübke, K., The Peptides, Vols. 1 and 2, Academic Press, New York and London, 1965 and 1966; Pettit, G. R., Synthetic Peptides, Vols. 1–4, Van Nostrand, Reinhold, New York 1970, 1971, 1975 and 1976; Houben-Weyl, Methoden der Organischen Chemie, Synthese von Peptiden, Band 15, Georg Thieme Verlag Stuttgart, NY, 1983; The Peptides, Analysis, synthesis, biology 1–7, Ed: Erhard Gross, Johannes Meienhofer, Academic Press, NY, San Fransisco, London; Solid phase peptide synthesis 2nd ed., John M. Stewaet, Janis D. Young, Pierce Chemical Company.

Thus, for example amine protecting groups which may be employed include protecting groups which may be employed include protecting groups such as carbobenzoxy (Z-), t-butoxycarbonyl (Boc-), 4-methoxy-2,3,6-trimethylbenzene sulphonyl (Mtr-), and 9-fluorenylmethoxycarbonyl (Fmoc-). It will be appreciated that when the peptide is built up from the C-terminal end, an amine protecting group will be present on the α-amino group of each new residue added and will need to be removed selectively prior to the next coupling step. One particularly useful group for such temporary amine protection is the Fmoc group which can be removed selectively by treatment with piperidine in an organic solvent.

Carboxyl protecting groups which may, for example be employed include readily cleaved ester groups such as benzyl (-OBZl), p-nitrobenzyl (-ONB), or t-butyl (-tOBu) as well as the coupling on solid supports, for example methyl groups linked to polystyrene.

Thiol protecting groups include p-methoxybenzyl (Mob), trityl (Trt) and acetamidomethyl (Acm).

It will be appreciated that a wide range of other such groups exists as, for example, detailed in the above-mentioned literature references, and the use of all such groups in the hereinbefore described processes fall within the scope of the present invention.

A wide range of procedures exists for removing amine- and carboxyl-protecting groups. These must, however, be consistent with the synthetic strategy employed. The side chain protecting groups must be stable to the conditions used to remove the temporary α-amino protecting groups prior to the next coupling step.

Amine protecting groups such as Boc and carboxyl protecting groups such as tOBu may be removed simultaneously by acid treatment, for example with trifluoro acetic acid. Thiol protecting groups such as Trt may be removed selectively using an oxidation agent such as iodine.

The cystein containing peptides may be synthesised by the methods described in the text with removal of all protecting groups including the thiol protecting groups as the last synthetic step.

The following Examples are given by way of illustration only.

Solvents were redistilled from commercial material and stored in the following way: Dimethylformamide (DMF) over molecular sieve 4A, dichloromethane (DCM) over CaCl$_2$, triethylamine (TEA) over Na/Pb alloy (Baker) and trifluoroacetic acid (TFA) over molecular sieve 4A.

TLC systems were as follows:

S$_1$: Silica/CHCl$_3$: MeOH (98:2)

S$_2$: Silica/CHCl$_3$: MeOH (95:5)

S$_3$: Silica RP 8/0.1% TFA in 5% EtOH (aq).

The purified end products were analyzed by reversed phase high performance liquid chromatography (HPLC). The HPLC-system consisted of a HP 1090M chromatograph with an in-built autosampler and a HP 1040 diode array (Hewlett-Packard, Waldbronn, FRG), and a supelcosil LC-18 column (250×4.6 mm, 5u particles). Samples were dissolved in 0.1% (v/v) TFA (aq) and eluted with a linear gradient from 0 to 30% acetonitrile in 0.1% TFA (aq.). The flow rate was 2 ml/min. The eluent was monitored at 214 nm with a bandwidth of 4 nm. The solvent chromatogram was electronically subtracted, and the results were presented in terms of area percent.

Amino acid analysis:

The cystine containing peptides were oxidized by performic acid to convert the acid labile cystine residue to the acid stable cysteic acid, before acid hydrolysis in 6M HCl at 110° C. for 16 hours. The dry hydrolysates were then derivatised by the use of phenyl isothiocyanate and analysed as described by Heinrikson (Anal. Bioch. 136, 65–74, 1984).

EXAMPLE 1

L-PYROGLUTAMYL-L-GLUTAMYL-L-ASPARTYL-L-CYSTEINYL-L-LYSINE: Compound (1)

(a) t-Boc-(S-p-METHOXYBENZYL)-L-CYSTEINYL-(ε-BENZYLOXYCARBONYL)-L-LYSINE BENZYLESTER (I)

ε-Benzyloxycarbonyl-lysine benzylester hydrochloride (406 mg) is dissolved in 3 ml of DMF and TEA is added until free TEA can be detected in the vapor phase with a wetted piece of pH indicator paper. To this solution t-Boc-(S-p-methoxybenzyl)-L-cysteine N-hydroxysuccinimide ester (491 mg) dissolved in 3 ml DMF is added. At appropriate time intervals portions of TEA are added to maintain the slight alkalinity of the solution. The mixture is left overnight at room temperature and after checking for a negative ninhydrin reaction is directly applied to a 2.5×75 cm column of Sephadex LH-20, equilibrated with DMF and calibrated with standard reactants (eg in the example given t-Boc-(γ-benzyl)-L-glutamic acid-p-nitrophenylester and p-nitrophenol). Column flow is maintained by gravity flow and the effluent is monitored at 280 nm before collection in fractions of approximately 10 ml. The product may be identified by t.l.c. of each fraction, the respective fractions being pooled and evaporated in vacuo; yield: 700 mg (100%) of an oily product, homogeneous in t.l.c. (chloroform/acetone (9/1)), $R_f$=0.64.

(b) t-Boc-(β-BENZYL)-L-ASPARTYL-(S-p-METHOXYBENZYL)-L-CYSTEINYL-(ε-BENZYLOXYCARBONYL)-L-LYSINE BENZYLESTER (II)

700 mg of the blocked and protected dipeptide (I) are dissolved in 25 ml of anhydrous DCM and 25 ml of anhydrous TFA are added. After 30 min acid and solvent are removed in vacuo. The residue is dissolved in DCM and again evaporated. To a solution of the residue in DMF (3 ml) which is made slightly alkaline with TEA a solution of t-Boc-(β -benzyl)-L-aspartic acid p-nitrophenylester (488 mg) in 3 ml DMF is added. Alkalinity should be frequently checked and maintained by additions of small amounts of TEA. After the ninhydrin reaction had become negative (after about 2 hrs) the reaction mixture is applied to a Sephadex LH-20 column (2.5×75 cm) and purified as described above. Yield after evaporation in vacuo; 900 mg (100%) of a crystalline product, homogeneous on t.l.c. (chloroform/acetone (9/1)), $R_f$=0.70.

(c) t-Boc-(γ-BENZYL)-L-GLUTAMYL-(β-BENZYL)-L-ASPARTYL-(S-p-METHOXYBENZYL)-L-CYSTEINYL-(ε -BENZYLOXYCARBONYL)-L-LYSINE BENZYLESTER (III)

900 mg of the blocked tripeptide derivative II are deblocked with TFA as described above, dissolved in 3 ml of DMF and made slightly alkaline with TEA. To this solution 504 mg of t-Boc-(γ-benzyl)-L-glutamic acid p-nitrophenylester (in 3 ml of DMF) are added. After about 2.5 hrs the ninhydrin reaction has become negative and the mixture is applied to a Sephadex LH-20 column for purification as described above. The separation of the components in this reaction mixture and its monitoring by t.l.c. may be carried out as above. The appropriate fractions (9–15 in this case) are pooled, evaporated and dried. Yield: 1140 mg (100%) of a pale yellowish oil, homogeneous on t.l.c. (chloroform/acetone (9/1)), $R_f$=0.53.

(d) BENZYLOXYCARBONYL-L-PYROGLUTAMYL-(γ-BENZYL)-L-GLUTAMYL-(β-BENZYL)-L-ASPARTYL-(S-p-METHOXYBENZYL)-L-CYSTEINYL-(ε-BENZYL-OXYCARBONYL)-L-LYSINE BENZYLESTER (IV)

1140 mg of the tetrapeptide derivative III are deblocked with TFA in DCM as described for I and dissolved in 3 ml DMF. The solution is made slightly alkaline with TEA and 423 mg of benzyloxycarbonyl-L-pyroglutamic acid p-nitrophenylester are added as a solution in 3 ml DMF. Alkalinity of the reaction mixture should be repeatedly checked and if necessary restored by addition of TEA. After about 3 hrs the ninhydrin test becomes negative and the pentapeptide derivative IV may be purified as described above. Yield 1230 mg (96%), pale yellowish oil, homogeneous on t.l.c. (chloroform/acetone (9/1)), $R_f$=0.44 (with tailing).

(e) L-PYROGLUTAMYL-L-GLUTAMYL-L-ASPARTYL-L-CYSTEINYL-L-LYSINE 50 mg of the protected pentapeptide derivative IV are dissolved in 50 ml liquid hydrogen fluoride at 0° C. with the addition of 500 mg methionine as a scavenger and left for 1 hour. The hydrogen fluoride is then evaporated to dryness in vacuo at 0° C. and the residue stirred with ethyl acetate, The ethyl acetate washing is decanted and discarded, The remaining material is dissolved in dilute acetic acid and lyophilised.

The lyophilised material (2 mg) may be purified by reversed phase HPLC using a C18-column 10 mm×10 cm at a flow rate of 2.8 ml per minute using gradient elution with solution A: 0.1% aqueous trifluoroacetic acid and solution B: 0.1% trifluoroacetic acid in acetonitrile; 0.10% of solution B being added over 30 minutes, Detection is effected using ultraviolet absorption at 214 nm or pyridine disulphide reagent (for SH-groups).

A number of further peptides may be synthesised by the general procedure of Example 1. These are identified and characterised in the following Table:

TABLE

| EXAMPLE | | AMINO ACID ANALYSIS | PURITY/HPLC |
|---|---|---|---|
| 2 | pGlu—Gln—Asp—Cys—Lys | Glu: 2.00; Asp: 1.07; Cys: 0.87; Lys: 1.15 | 95% |
| 3 | Ac—Glu—Glu—Asp—Cys—Lys | Glu: 2.00; Asp: 1.11; Cys: 0.84; Lys: 1.11 | 94% |
| 4 | pGlu—Glu—Glu—Cys—Lys | Glu: 2.98; Cys: 1.00; Lys: 1.19 | 93% |
| 5 | pGlu—Glu—Asp—Cys—D—Ala—Lys | Glu: 1.99; Asp: 1.00; Cys: 0.89; Lys: 1.12; Ala: 1.01 | 94% |
| 6 | pGlu—Glu—Asp—Cys—Lys—$NH_2$ | Glu: 2.00; Asp: 1.07; Cys: 0.87; Lys: 1.14 | 94% |
| 7 | pGlu—Asp—Asn—Cys—Lys | Glu: 0.94; Asp: 2.00; Cys: 0.85; Lys: 1.10 | 96% |
| 8 | pGlu—Glu—Asp—Cys—Gly—Lys | Glu: 2.05; Asp: 0.90; Cys: 0.95; Lys: 0.99; Gly: 1.07 | 98% |
| 9 | pGlu—Glu—Asp-(Benzyl-Cys)—Lys | Glu: 1.91; Asp: 1.06; Cys: —; Lys: 1.00; | 99% |
| 10 | pGlu—Ala—Asp-(Benzyl-Cys)—Lys | Glu: 1.00; Asp: 1.00; Cys: 1.13; Lys: 0.97; Ala: 0.97 | 95% |
| 11 | pGlu—Ala—Asp—Cys—Lys | Glu: 1.08; Asp: 0.95; Cys: 0.99; Lys: 1.03; Ala: 0.94 | 98% |
| 12 | pGlu—D—Ala—Asp—Cys—Lys | Glu: 1.10; Asp: 0.95; Cys: 0.89; Lys: 1.03; Ala: 0.92 | 98% |
| 13 | Gln—Glu—Asp—Cys—Lys | Glu: 2.00; Asp: 0.98; Cys: 0.81; Lys: 1.16 | 97% |
| 14 | pGlu—Glu—Asp—Cys—Gly | NO DATA | 88% |
| 15 | pGlu—Glu—Asp-(2-pyridylthio-Cys)Lys | NO DATA | 97% |
| 16 | pGlu—Gly—Asp-(Benzyl-Cys)—Lys | Glu: 1.00; Asp: 1.00; Cys: 1.16; Lys: 0.99; Gly: 1.04 | 98% |
| 17 | pGlu—Glu—Glu-(Benzyl-Cys)—Lys | Glu: 3.00; Cys: 1.1 ; Lys: 1.0; | 93% |
| 18 | pGlu—Gly—Asp—Phe—Lys | Glu: 1.00; Asp: 1.00; Gly: 1.00; Phe: 1.00; Lys: 1.00 | 99% |
| 19 | pGlu—Gly—Asn—Cys—Lys | Glu: 2.10; Asp: 1.00; Cys: 1.00; Lys: 1.00 | 70% |
| 20 | pGlu—Gln—Asn—Cys—Lys | Glu: 2.06; Asp: 0.94; Cys: 1.01; Lys: 0.99 | 75% |
| 21 | pGlu—Glu—Asp—Ser—Lys | NO DATA | >92% |
| 22 | pGlu—Gly—Asp—Cys—Lys | NO DATA | >95% |
| 23 | pGlu—Asp—Asp—Cys—Lys | Glu: 1.92; Asp: 1.08; Cys: 1.02; Lys: 1.00 | 100% |
| 24 | pGlu—Asp—Asp—Cys—Arg | Glu: 1.96; Asp: 1.12; Cys: 1.00; Arg: — | 99% |
| 25 | Glu—Glu—Asp—Cys—Lys | Glu: 2.00; Asp: 0.98; Cys: 0.81; Lys: 1.10 | 97% |
| 26 | Pro—Glu—Asp—Cys—Lys | Glu: 0.99; Asp: 1.04; Cys: 1.01; Lys: 0.99; Pro: — | 98% |
| 27 | pGlu—Glu—Glu—Cys—Arg | Glu: 2.93; Cys: 1.01; Arg: 1.03 | 100% |
| 28 | Ser—Glu—Glu—Glu—Cys—Arg | Glu: 2.98; Ser: 0.97; Cys: 0.98; Arg: 1.08 | 95% |
| 29 | Ser—Gln—Glu—Glu—Cys—Arg | Glu: 2.96; Ser: 0.96; Cys: 0.96; Arg: 1.11 | 98% |

The peptides were characterized by TLC, HPLC and amino acid analysis.

EXAMPLE 30 pGlu-Glu-Asp-Ser-Lys-OH

The peptide was synthesised on a LKB Biolynx 4170 fully automatic peptide synteseizer with monitoring at UV 304 nm. Fmoc was used as temporary N-protection and UV tracer. The C-terminal amino acid was linked to the polymer via an acid labile spacer anm, Standard protocol was:

| | |
|---|---|
| Couping with recirculation | 30 min. |
| Wash with DMF | 10 min. |
| Deprotection with 20% piperidine/DMF | 10 min. |
| Wash with DMF | 10 min. |

The C-terminal amino acid was activated as symmetrical anhydride with DCC and coupled to the polymer with N,N-dimethylaminopyridine as catalyst. After recirculation for 60 min. standard procedure was used during the entire synthesis.

Amino acid derivatives used:

Fmoc-Lys($\epsilon$-N-Boc)-OH
Fmoc-Ser (O-tBu)-ODBH
Fmoc-Asp($\beta$-tOBu)-OPfp
Fmoc-Glu($\upsilon$-tOBu)-OPfp
pGlu-OPC1P After final wash of the fully protected pentapeptide, the polymer was washed with diethylether and air dried.

The peptide was fully deprotected and split from the polymer in one operation by treatment with 95% aq. TFA for 1 h. After filtration, wash with TFA and evaporation, the final peptide was purified on a RP 8 column and eluted with ethanol in 0.1% TFA.

Yield: 44% Purity: More than 92% (HPLC RP18, 214 nm). Amino acid analysis: Acceptable.

I claim:

1. A method of inhibiting proliferation of epidermal or epithelial stem cells in a human or animal subject which comprises administering to the human or animal subject an effective amount of a compound of formula (I):

$$R^a\text{-}R^b\text{-}R^c\text{-}R^d\text{-}(R^e)_n\text{-}R^f \qquad (I)$$

wherein:

$R^a$ represents

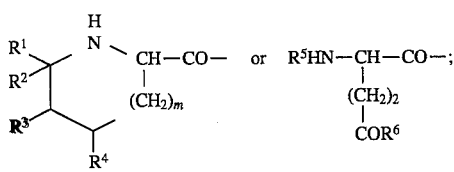

$R^b$ represents

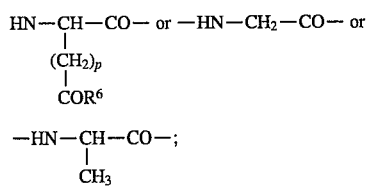

$R^c$ represents

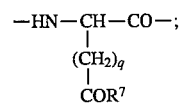

$R^d$ represents

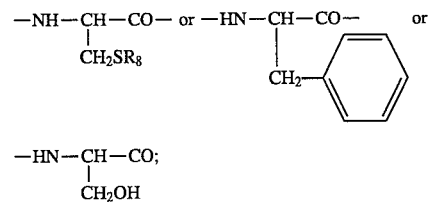

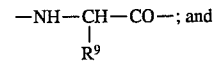

$R^e$ represents

—NH—CH—CO—; and
      |
      $R^9$ $R^f$ represents

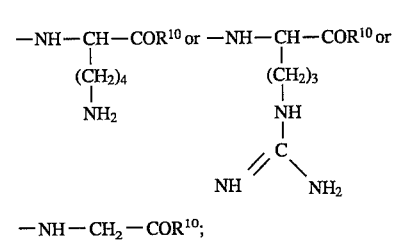

—NH—CH$_2$—COR$^{10}$;

wherein:
  n and m independently represent 0 or 1;
  p and q independent represent 1 or 2;
  $R^1$ and $R^2$ are both hydrogen atoms or together represent an oxo group;
  $R^3$ and $R^4$ are both hydrogen atoms or together represent a carbon—carbon bond;
  $R^5$ is hydrogen or an acyl group;

$R^6$ and $R^7$ independently represent a hydroxy group or an amino group;

$R^8$ represents hydrogen; a $C_{2-6}$alkyl group; a $C_{7-20}$aralkyl group, which may carry one or more hydroxy, amino or methoxy substituents; or a metabolically labile S-protecting group;

$R^9$ represents hydrogen or a methyl group;

$R^{10}$ represents a hydroxy or amino group, the residue of the amino acid glutamine or a peptide having an N-terminal glutamine unit;

and wherein, apart from alanine, which may be in the D or L form, and glycine, all the said amino acid residues are in the L-form, with the proviso that when $R^d$ represents serine and n is zero, $R^f$ is lysine or arginine, or an amide thereof.

2. A method of controlling proliferation of epidermal or epithelial stem cells in a human or animal subject which comprises administering to the human or animal subject an effective amount of a compound of formula (I) as claimed in claim 1, with the proviso that the compound is other than
pGlu-Asp-Asp-Cys-Lys,
pGlu-Glu-Asp-Cys-Lys,
pGlu-Gln-Asp-Cys-Lys,
pGlu-Glu-Asp-Cys-Gly-Lys,
pGlu-Glu-Asp-Cys-Ala-Lys, or
pGlu-Glu-Asp-Cys-LysNH$_2$.

3. A compound of formula (II):

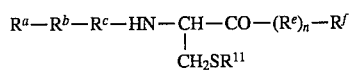

wherein $R^a$ represents

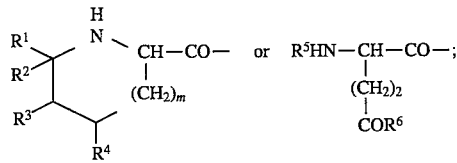

$R^b$ represents

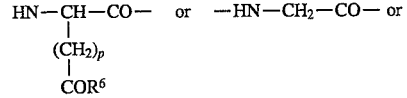

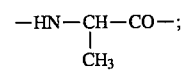

$R^c$ represents

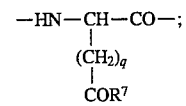

$R^e$ represents

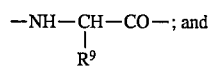

$R^f$ represents

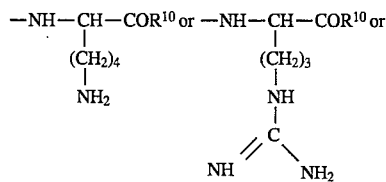

wherein:

n and m independently represent 0 or 1;

p and q independent represent 1 or 2;

$R^1$ and $R^2$ are both hydrogen atoms or together represent an oxo group;

$R^3$ and $R^4$ are both hydrogen atoms or together represent a carbon—carbon bond;

$R^5$ is hydrogen or an acyl group;

$R^6$ and $R^7$ independently represent a hydroxy group or an amino group;

$R^9$ represents hydrogen or a methyl group;

$R^{10}$ represents a hydroxy or amino group, the residue of the amino acid glutamine or a peptide having an N-terminal glutamine unit; and $R^{11}$ is a $C_{2-6}$alkyl or a $C_{7-20}$aralkyl group which may carry one or more hydroxy, amino or methyl substituents;

and wherein, apart from alanine, which may be in the D or L form, and glycine, all the said amino acid residues are in the L-form.

4. A compound of formula (III):

$$R^a—R^b—R^c—HN—CH—CO—(R^e)_n—R^f \quad (III)$$
$$|$$
$$CH_2—C_6H_5$$

$R^a$ represents

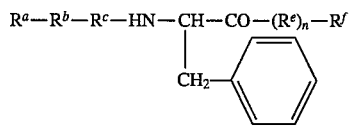

$R^b$ represents

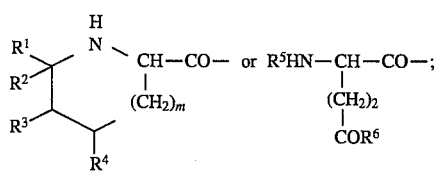

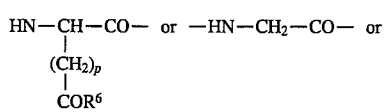

$R^c$ represents

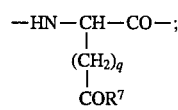

$R^e$ represents

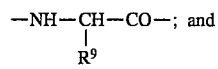

$R^f$ represents

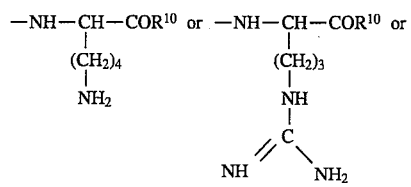

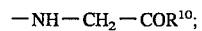

wherein:

n and m independently represent 0 or 1;

p and q independent represent 1 or 2;

$R^1$ and $R^2$ are both hydrogen atoms or together represent an oxo group;

$R^3$ and $R^4$ are both hydrogen atoms or together represent a carbon—carbon bond;

$R^5$ is hydrogen or an acyl group;

$R^6$ and $R^7$ independently represent a hydroxy group or an amino group;

$R^9$ represents hydrogen or a methyl group; and $R^{10}$ represents a hydroxy or amino group, the residue of the amino acid glutamine or a peptide having an N-terminal glutamine unit;

and wherein, apart from alanine, which may be in the D or L form, and glycine, all the said amino acid residues are in the L-form.

5. A compound of formula (IV):

$$R^a—R^b—R^c—NH—CH—CO—(R^e)_n—R^f \quad (IV)$$
$$|$$
$$CH_2SR^{12}$$

$R^a$ represents

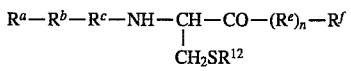

$R^b$ represents

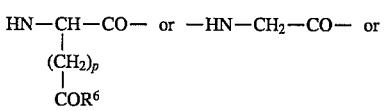

-continued

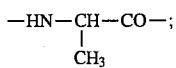

$R^c$ represents

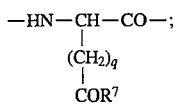

$R^e$ represents

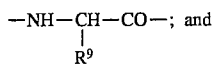

$R^f$ represents

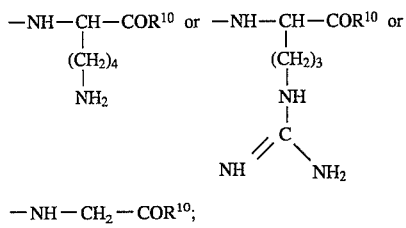

—NH—CH$_2$—COR$^{10}$;

wherein:

n and m independently represent 0 or 1;

p and q independent represent 1 or 2;

$R^1$ and $R^2$ are both hydrogen atoms or together represent an oxo group;

$R^3$ and $R^4$ are both hydrogen atoms or together represent a carbon—carbon bond;

$R^5$ is hydrogen or an acyl group;

$R^6$ and $R^7$ independently represent a hydroxy group or an amino group;

$R^9$ represents hydrogen or a methyl group;

$R^{10}$ represents a hydroxy or amino group, the residue of the amino acid glutamine or a peptide having an N-terminal glutamine unit; and $R^{12}$ is a metabolically labile S protecting group;

and wherein, apart from alanine, which may be in the D or L form, and glycine, all the said amino acid residues are in the L-form.

6. A compound of formula (V):

R$^a$-HN-CH$_2$-CO-R$^c$-R$^d$-(R$^e$)$_n$-R$^f$   (V)

wherein

R$^a$ represents

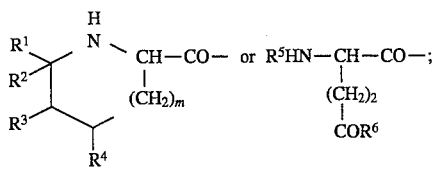

R$^c$ represents

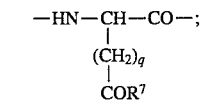

R$^d$ represents

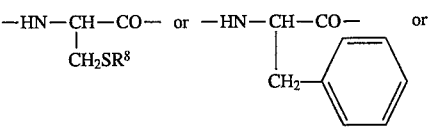

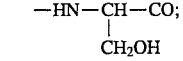

R$^e$ represents

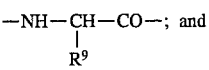

R$^f$ represents

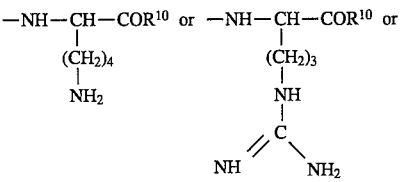

—NH—CH$_2$—COR$^{10}$;

wherein:

n and m independently represent 0 or 1;

q represents 1 or 2;

$R^1$ and $R^2$ are both hydrogen atoms or together represent an oxo group;

$R^3$ and $R^4$ are both hydrogen atoms or together represent a carbon—carbon bond;

$R^5$ is hydrogen or an acyl group;

$R^6$ and $R^7$ independently represent a hydroxy group or an amino group;

$R^8$ represents hydrogen; a C$_{2-6}$alkyl group; a C$_{7-20}$aralkyl group, which may carry one or more hydroxy, amino or methoxy substituents; or a metabolically labile S-protecting group;

$R^9$ represents hydrogen or a methyl group;

$R^{10}$ represents a hydroxy or amino group, the residue of the amino acid glutamine or a peptide having an N-terminal glutamine unit;

and wherein, apart from alanine, which may be in the D or L form, and glycine, all the said amino acid residues are in the L-form, with the proviso that when R$^d$ represents serine and n is zero, R$^f$ is lysine or arginine, or an amide thereof.

7. A compound of formula (VI):

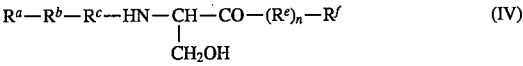

R$^a$ represents

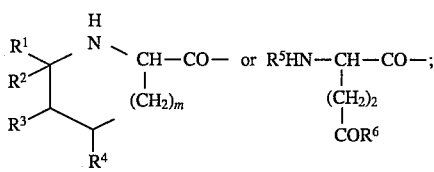

$R^b$ represents

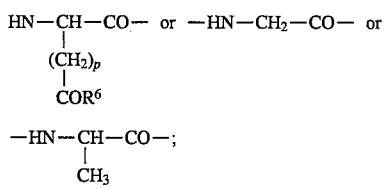

$R^c$ represents

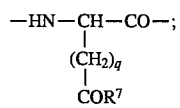

$R_e$ represents

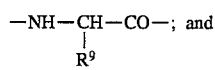

$R^f$ represents

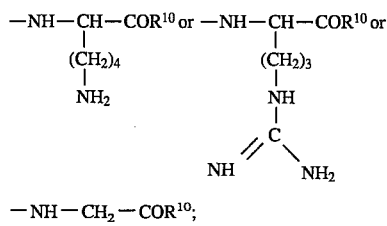

$-NH-CH_2-COR^{10}$;

wherein:

n and m independently represent 0 or 1;

p and q independent represent 1 or 2;

$R^1$ and $R^2$ are both hydrogen atoms or together represent an oxo group;

$R^3$ and $R^4$ are both hydrogen atoms or together represent a carbon—carbon bond;

$R^5$ is hydrogen or an acyl group;

$R^6$ and $R^7$ independently represent a hydroxy group or an amino group;

$R^9$ represents hydrogen or a methyl group; and $R^{10}$ represents a hydroxy or amino group, the residue of the amino acid glutamine or a peptide having an N-terminal glutamine unit;

and wherein, apart from alanine, which may be in the D or L form, and glycine, all the said amino acid residues are in the L-form, with the proviso that, when n is zero, $R^f$ is lysine or arginine, or an amide thereof.

8. A method of inhibiting epidermal or epithelial cell proliferation in a human or animal subject comprising administering to the human or animal subject an effective amount of a compound of formula (VI) as claimed in claim 7.

9. A method of inhibiting proliferation of epidermal or epithelial stem cells in a human or animal subject comprising administering to the human or animal subject an effective amount of a compound of formula (II) as claimed in claim 3.

10. A method of inhibiting proliferation of haemopoietic, epidermal or epithelial stem cells in a human or animal subject comprising administering to the human or animal subject an effective amount of a compound of formula (III) as claimed in claim 4.

11. A method of inhibiting proliferation of epidermal or epithelial stem cells in a human or animal subject comprising administering to the human or animal subject an effective amount of a compound of formula (IV) as claimed in claim 5.

12. A method of inhibiting proliferation of haemopoietic, epidermal or epithelial stem cells in a human or animal subject comprising administering to the human or animal subject an effective amount of a compound of formula (V) as claimed in claim 6.

* * * * *